United States Patent [19]

Liss et al.

[11] Patent Number: 5,421,817
[45] Date of Patent: Jun. 6, 1995

[54] NON-INTRUSIVE ANALGESIC NEUROAUGMENTIVE AND IONTOPHORETIC DELIVERY APPARATUS AND MANAGEMENT SYSTEM

[75] Inventors: Saul Liss; Bernard Liss, both of Glen Rock, N.J.

[73] Assignee: E.P., Inc., N.J.

[21] Appl. No.: 127,163

[22] Filed: Sep. 27, 1993

Related U.S. Application Data

[63] Continuation-in-part of Ser. No. 877,873, May 4, 1992, abandoned, which is a continuation of Ser. No. 703,610, May 21, 1991, Pat. No. 5,109,847.

[51] Int. Cl.$^6$ ............................................. A61N 1/30
[52] U.S. Cl. ................................................ 604/20
[58] Field of Search ........................................ 604/20

[56] References Cited

U.S. PATENT DOCUMENTS 5,135,478  8/1992  Sibalis .................................. 604/20
5,312,325  5/1994  Sibalis .................................. 604/20

Primary Examiner—William E. Kamm
Assistant Examiner—Scott M. Getzow
Attorney, Agent, or Firm—Hopgood, Calimafde, Kalil & Judlowe

[57] ABSTRACT

The present invention pertains to a portable non-invasive electronic apparatus which can be used to relieve pain or alter the symptoms of certain neurological dysfunctions. A specifically contoured constant current and current limited waveform is generated and applied to selectively positioned electrodes. A program controlled processor tracks usage of the unit to prevent abuse and monitor progress. An overall treatment regimen centered on the stimulator may be effected simply and safely. The invention also provides an apparatus and method for the iontophoretic topical administration of a pharmaceutical agent. The apparatus is operated in a monopolar mode with a particular complex waveform which synergistically enhances the amount of various neurobiochemical species in the cerebral spinal fluid and the blood plasma.

8 Claims, 4 Drawing Sheets

CARRIER FREQUENCY
15,000 hz MONOPOLAR
FIG. IA
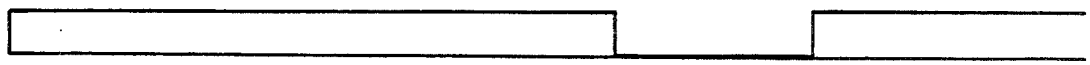
1st MODULATOR
15 hz
FIG. IB
2nd MODULATOR
500 hz
FIG. IC
TYPICAL COMBINED
WAVEFORM (MONOPOLAR)
FIG. ID
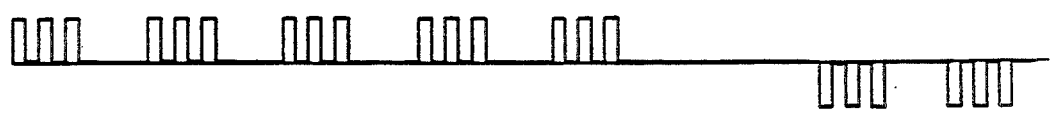
TYPICAL COMBINED
WAVEFORM (BIPOLAR)
FIG. IE

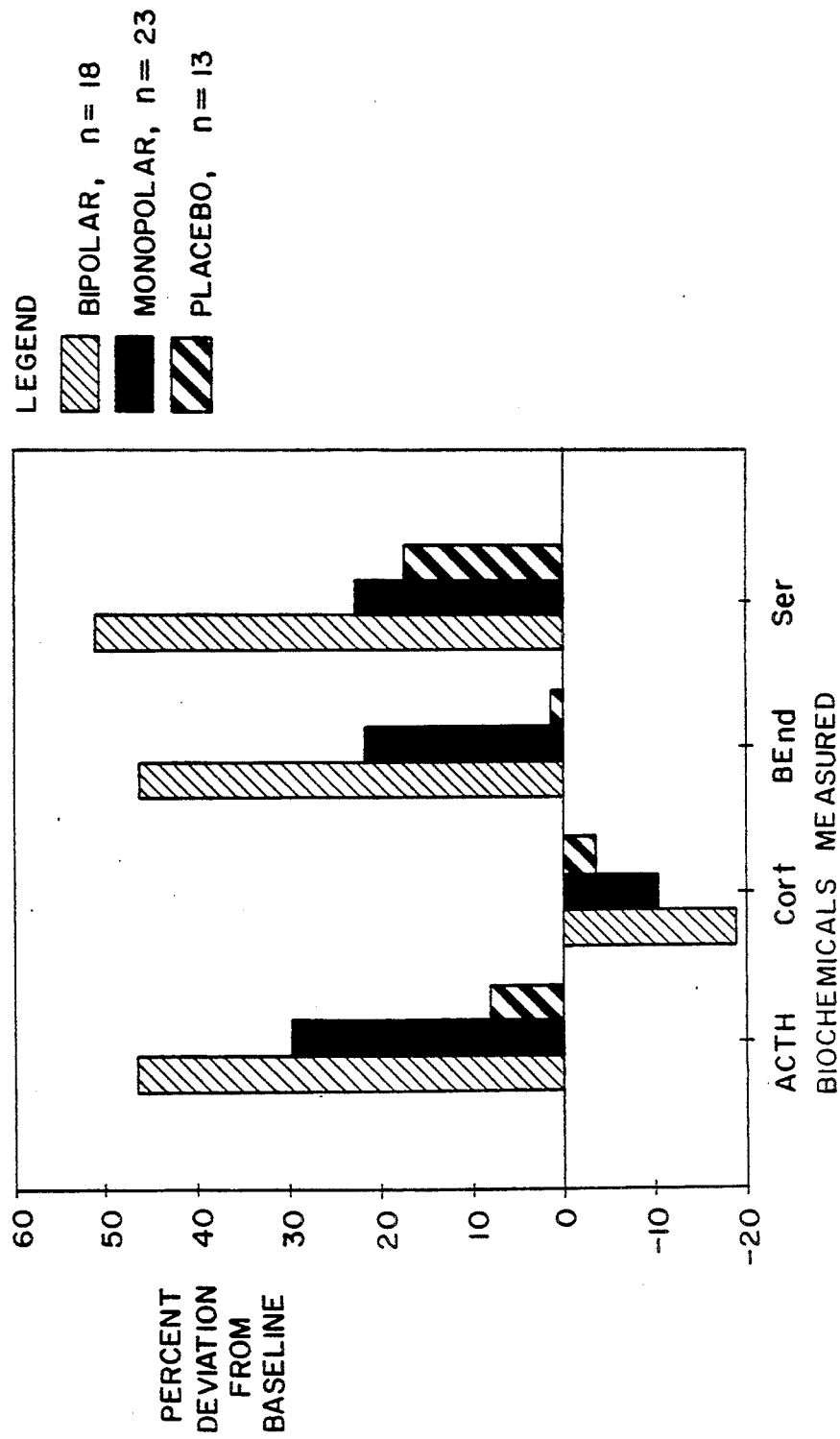

NON-INTRUSIVE ANALGESIC NEUROAUGMENTIVE AND IONTOPHORETIC DELIVERY APPARATUS AND MANAGEMENT SYSTEM

This application is a continuation-in-part of application Ser. No. 877,873, filed May 4, 1992, now abandoned, which is a continuation of application Ser. No. 703,610, filed May 21, 1991, now U.S. Pat. No. 5,109,847, the disclosures of which are incorporated herein by reference.

BACKGROUND OF THE INVENTION

1. The Field of the Invention

The invention of our prior application, now U.S. Pat. No. 5,109,847, generally relates to an apparatus that modulates the neurological responses associated with certain biological dysfunctions and neural pain, pain caused by blood flow deficiency and more specifically, is an apparatus and system for the treatment of selected pain and/or neural dysfunction induced maladies.

The present invention is an improvement thereof, and relates to an apparatus for the topical iontophoretic administration of medication in the treatment of various conditions.

2. The State of the Art

The sensation of pain is associated with numerous physiological and psychological ailments and is a universal experience of all complex living organisms. Pain, as the mental manifestation of a neurological response, is an important biological attribute and critical to living and adapting to the environment. Notwithstanding this important role, the alleviation of pain has been a fundamental goal of medicine for as long as the medical profession has existed. Indeed, the ability to control the neurological pathways through which pain is conveyed, has made complex procedures far simpler to implement and much less traumatic to the patient.

There is additionally a class of neurological response which is associated with pain that does not correspond to or act as a warning for a particular physical damage or biological dysfunction. In fact, many biologically important transitions are characterized by significant pain, such as the withdrawal period of an addict, during which time the addict's system is depleted of a specific endogenous narcotic. Other mental conditions which are neurological response dependent conditions include depression, hypertension, causalgia pain, insomnia and jet lag.

The importance of the ability to control neurological response and associated perceptions of pain and distress has led to the development of many pain control methodologies. The most common of which employs bioactive chemical agents that act to block neural transmission pathways within the body. These are designed to operate locally for spot treatment or broadly for generalized control or inhibition of pain response throughout the body. Chemical interference with pain signals has broad based appeal, but in many instances is unacceptable. For example, certain chemicals have toxic side affects or cause allergic reactions to certain patients. For more chronic ailments, such as chronic migraine headache syndrome, continuous absorption of chemical narcotics may reduce the associated pain, but at unacceptable high costs associated with interference with routine activities, addiction and/or toxicity of the narcotic.

In view of the problems associated with chemical pain control, efforts have abounded to discover treatment approaches which would not involve pharmacological (chemical) interference with neural transmitters in the body. One approach that has recently sparked tremendous interest is the use of low power electrical stimulator devices capable of passing currents across key neural transmitter junctions in the body and thus effecting a blockage of neurological pathways which are inducing messages of pain to the brain. A practical implementation of this approach is disclosed in U.S. Pat. No. 3,902,502 to Liss, et al; the teachings of which are herein incorporated by reference.

The system disclosed in the '502 patent presented a pulsed direct current waveform having a high frequency carrier modulated by a single low frequency modulation. It was discovered that this waveform was particularly successful at controlling symptoms of certain neurological disorders.

Although effective for its applied treatment, many electrical stimulatory devices are limited to certain applications and lack the requisite flexibility for broad-based appeal. In addition, a drawback to the use of electrical stimulation to control pain is the concern by patients and others about the impact of power dissipation on the patient. Although low current, the power dissipation of many of the electrical stimulation devices is still quite significant. Efforts to reduce the applied power have resulted in stimulation devices with little or no physiological impact.

There has been, therefore, a search for new electrical stimulation devices characterized by exceptional pain management capabilities while reducing the overall patient exposure to electrical energy.

It is also clear that pain can be caused by organic physiologic conditions, trauma, infections, and the like. While systemic analgesic agents have been used with some success, it is often desirable to attempt administration directly to the area of the patient the medication is required. This concept also has applications in the administration of quite a wide variety of pharmacological agents. For example, Joseph Kleinkort delivered a presentation almost a decade ago at the USAFE Medical Convention in Garmisch, Germany, in which he described iontophoretic administration of hydrocortisone; the technique was referred to as transionic injection. Using two moistened electrodes and a particular type of micronized hydrocortisone dispersed in a petrolatum ointment base, he found that transonic injection was as effective as percutaneous injection. The apparatus used by Kleinkort provided an electrical waveform to the electrodes which consisted of a carrier frequency of 12-20 KHz and a modulation frequency of 8-20 Hz.

More recently, Sibalis in U.S. Pat. No. 5,135,478, the disclosure of which is incorporated herein by reference, described an electrical transdermal drug applicator which provides a particular waveform to counteract the apparent decrease in the amount of the pharmaceutical delivered as the duty cycle of the apparatus (i.e., the time during which current is "on" relative to the time current is "off") increases. Sibalis provides a waveform to the electrodes which comprises a negative conditioning pulse and a sequence of different waveforms which dilate blood vessels, impede coagulation and vasoconstriction, and thereby allow for better transdermal delivery of the drug. The complex waveform generally uses an AC carrier frequency of 1.5-3.5 MHz, a pulse width of 1.25-11.25 ms, and is modulated by both an AC modulated square wave at 250 Hz and a second AC modulator at 570-870 Hz.

There is yet a need for the improved transdermal delivery of drugs, including improved tissue wetting management, minimization of the amount of electrical energy delivered to the patient, improved patient response and comfort with the procedure, and there is especially a need to tailor the aspects of delivery with respect to the particular drug or combinations of drugs used.

SUMMARY AND OBJECTS OF THE PRESENT INVENTION

This invention may be summarized, at least in part with reference to its objects.

It is, therefore, an object of the present invention to provide an apparatus for the selective generation of low current nerve stimulation waveforms configured to control pain and/or reduce the specific symptoms of certain neurological dysfunctions.

It is another object of the present invention to provide an apparatus for generating a complex waveform that when applied to a patient involves very low power dissipation.

It is a further object of the present invention to provide a pain control system that includes a means for creating a complex waveform and a data processing means for managing and recording the implementation of that waveform.

It is yet another object of the present invention to provide a method for low power, electrically induced analgesic treatment by the placement of at least two electrodes on selected neurologically important sites and the controlled introduction of a complex waveform for a predetermined time forming a treatment regimen.

It is still another object of the present invention to provide a method for treating the neurological dysfunctions associated with such ailments as migraine headaches, dental procedures, PMS and drug withdrawal.

The above and other objects of the present invention are realized in a specific illustrative electrical stimulator device. This device includes a small DC power source and a means for converting the current output of the power source into a complex waveform as an output across two or more electrodes attached to the patient's body. The complex waveform includes a carrier frequency with at least two low frequency modulations. The carrier frequency will range between 1 and 100,000 kilohertz. The first modulation to this carrier will have a frequency between 0.01 and 199 kilohertz. The second modulation to the carrier will have a frequency range between 0.1 and 100 kilohertz. Each modulation to the carrier is a pulse train in the form of a square waveform.

The placement of the electrodes will depend on the ailment of the subject of treatment, and the frequency of treatment will depend on the severity of the pain or dysfunction.

In accordance with the varying aspects of the present invention, the stimulator device may include a digital data processor and stored programming for enhanced implementation of the prescribed treatment. In this manner, the program controlling the output of the stimulator will prevent use beyond a number of times and beyond the time set for each use. The limits of number of uses and of length of time for each use will be set by the prescribing physician. This promotes and enhances the use of expressly developed treatment regimens by a prescribing physician. The patient's progress can be compared to patient compliance in the context of continuing the prescription or altering same on behalf of the patient.

In our improved invention, one object is provide an improved tissue-electrode interfacial environment to provide the transdermal delivery of the pharmaceutical agent.

Another object of our invention is to minimize the amount of electrical energy which must be applied to the patient to enable a suitable dosage of the drug to be administered.

Yet another object of the invention is to avoid harsh sensation response to the electrical energy, thereby improving patient comfort and compliance with the procedure.

Still another object of the invention is to tailor the characteristics of the electrical energy to the particular drug being administered to the patient to enhance the administration and/or the efficacy of the drug delivered.

In particular, the present invention provides an improved apparatus which comprises the aforementioned electrical stimulator device having two moist electrodes, at least one of which contains a pharmaceutical agent in a suitable carrier. The complex waveform used during iontophoretic transdermal administration includes a carrier signal operating at 1-300 GHz, a first modulating frequency operating at 0.01-199 KHz (10-199,000 Hz), and a second modulation frequency operating at 100 Hz-300 GHz. The waveform is monopolar.

The foregoing features of the present invention may be more fully understood in view of a specific illustrative embodiment thereof presented herein below in conjunction with the following drawings of which:

BRIEF DESCRIPTION OF THE FIGURES

FIGS. 1A-1E depict sample simple and combined waveforms utilized in the present invention, particularly a monopolar carrier waveform (FIG. 1A), modulator waveforms of different frequencies (FIGS. 1B and 1C), and combined monopolar and bipolar waveforms (FIGS. 1D and 1E, respectively).

FIG. 4 is a chart of the effect of the inventive apparatus on certain neurotransmitters.

DESCRIPTION OF THE PREFERRED EMBODIMENT

Figure 2:
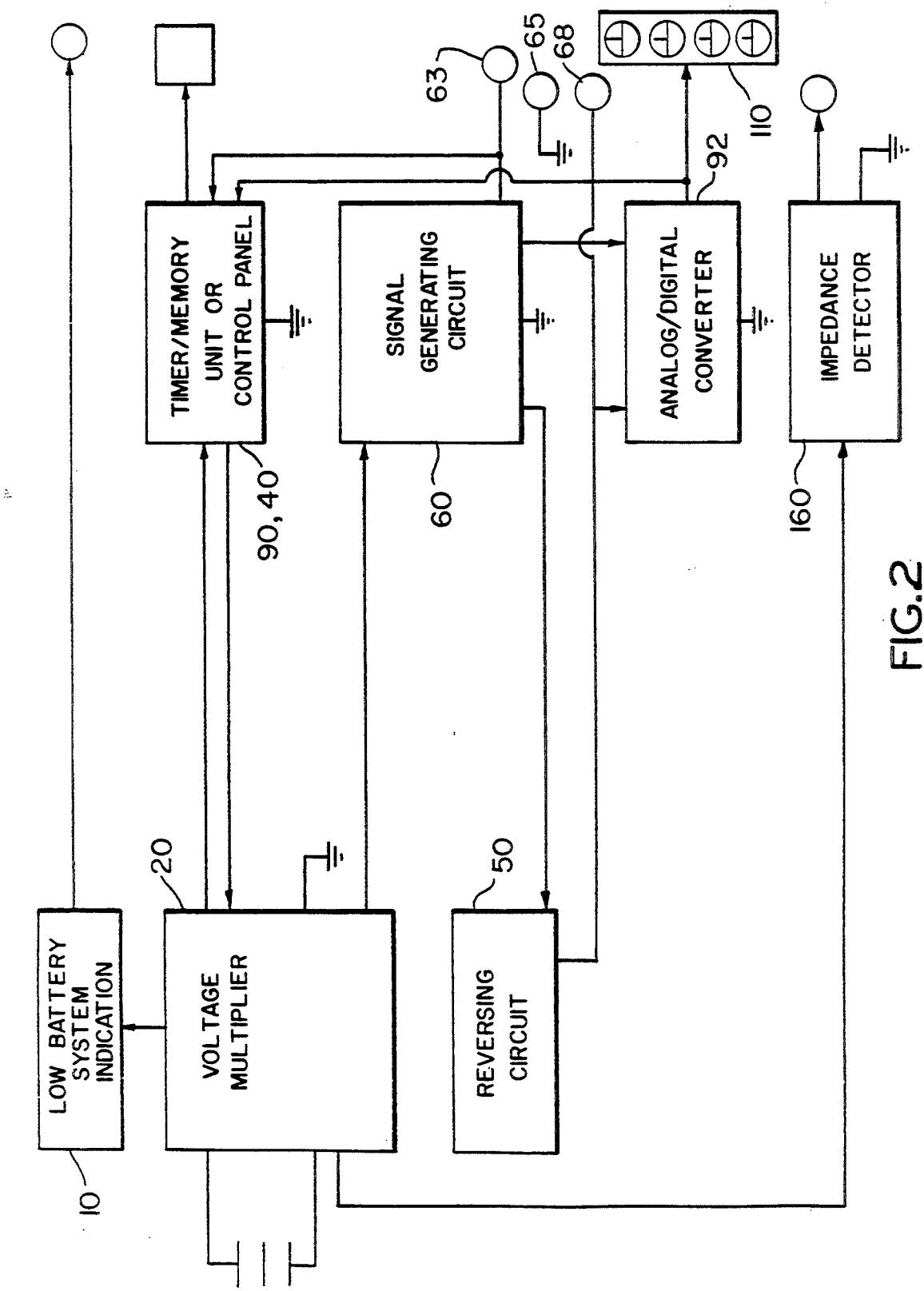
FIG. 2 is a block diagram of the inventive apparatus for generating the waveform depicted in FIG. 1.

Discussing the present invention first in overview, it is a fundamental diserratum to provide a portable non-invasive analgesia inducing apparatus that exhibits a selectively developed complex waveform for an electrical output. This output is applied between at least two contact probes for generating intracorporal current. The placement of the probes will depend on the treatment regimen. For example, migraine headache syndrome may involve the placement of the contacting probes on each side of the patient's cranium, one at the primary site of pain and the second at the contralateral trapezius insertion. Other locations may include intraoral e.g., for local analgesia to control the pain associated with a dental restoration procedure.

Although the theory describing the underlying pain control phenomenon is not well known or, for that matter, even established, it is generally believed that the introduction of an intracorporal current acts upon the electrically conducted neural transmitters of the patient. It has been discovered that the particular complex waveform of the present invention when applied to a patient creates distinct changes in the blood plasma and cerebral spinal fluid concentration of such compounds as melatonin, serotonin, beta endorphin, norepinephrine and cholinesterase which are highly correlated with the pain/pleasure centers of the central nervous system.

In operation, the present invention involves two functional attributes. The first involves the generation of the complex waveform of a select signature. The second attribute is directed to the implementation of the treatment in a delineated treatment regimen.

With the above overview in mind, attention is first directed to FIG. 1 which presents the various components of the complex waveform of the present invention. More particularly, and starting with FIG. 1A, a graphical representation is provided of the carrier frequency for one specific time segment. In this representation, the carrier frequency equals 15 kilohertz. The amplitude is volts (DC) and a duty cycle of 50%. The waveform contains 25 bursts of 15 pulses for each burst. The period for each burst is 2 milliseconds and the period for each pulse is 66.7 microseconds. For each, the burst and the pulse, the duty cycle is 50% on time. Continuing in FIG. 1, FIG. 1B presents the first modulation to the carrier frequency. In this example, the first modulation has a frequency of 15 Hertz and a duty cycle of 0.75. The second modulation is depicted in FIG. 1C. The second modulation has a frequency of 500 Hertz and a 50% duty cycle. Continuing through FIG. 1 and specifically FIG. 1D, the waveform combining the components depicted in FIGS. 1A through C above is presented.

The complex waveforms of the present invention may be generated with sinusoidal, sawtooth, hyperbolic or other wave shapes; for clarity, the waveforms presented in FIG. 1 and further discussed below have been exemplified by a simple square wave.

A cycle for the waveform will consist of 50 milliseconds "on" time in which the pulses for that frequency combination are generated and then there will be an "off" time of 16.7 milliseconds.

Finally, in FIG. 1E, a complex waveform according to the present invention is provided, wherein the polarity of the output is switched from positive to negative on a periodic basis, e.g., 67 milliseconds. This is contrasted with the waveform of FIG. 1D in which the polarity remains positive throughout the cycle; the pulsed DC waveform of FIG. 1D is considered a monopolar output while the output depicted in FIG. 1E is considered bipolar.

For purposes of rough approximation, the energy dissipation in using the present invention is represented by the area under the pulses depicted in FIG. 1D. It can, therefore, be recognized that by adding the second modulation, having a 50% duty cycle, results in a 50% decrease in power dissipation.

The circuit is presently provided with one of the following frequency combinations but not limited to:
1) 15 Hz, 500 Hz, 15,000 Hz—Monopolar;
2) 15 Hz, 500 Hz, 15,000 Hz—Bipolar (7.5 Hz);
3) 15 Hz, 500 Hz, 60,000 Hz—Monopolar; or
4) 15 Hz, 4,000 Hz, 60,000 Hz—Monopolar.

Turning now to FIG. 2, the functional elements of the inventive device are presented. The power source to the present system will either be a battery having a nominal 9 volt terminal voltage (or other suitable voltage) or some rectified and properly transformed line (AC) power source. The battery provides the basic DC power source for generating the complex waveform. This is channeled and controlled by the voltage multiplier 20. The output of the voltage multiplier 20 which is between 27 v to 40 v, is fed to signal generating circuit 60 which is the oscillating circuit that converts the constant DC output into the complex waveform having the desired characteristics.

The specific constant current and current limited waveform generated by signal generating circuit 60 is pre-set by entering the various frequency settings for the two modulations, and the carrier. This may be entered manually through adjusting the settings on control panel 90. Alternatively, these settings may be stored in digital memory 40 as previously set values. The actual output of this system is regulated by monitor 70 which then provides the system output on a display, via control panel 90, or a memory value for subsequent retrieval from memory 40.

The signal generating circuit 60 receives the voltage of 27 v to 40 v from the voltage multiplier. Within the signal generating circuit 60, the voltage branches off into a carrier frequency and two modulation frequencies. An example of the branching of the waveform is described in FIG. 1.

In FIG. 2, the system supports two separate probes for placement on the patient. Probe 63 represents the positive terminal as generated by signal generating 60. The second probe 65, is grounded within the circuit. For operation applying a bipolar waveform, the probes are connected to terminal 65 and 68, respectively. Terminal 68 is the output from reversing circuit 50, which may be present and which acts to flip the signal generating circuit pursuant to pre-set timing constraints.

The following ancillary systems are also present in this circuit. The "low battery" and "system on" indicator 10 which monitors the battery output via voltage multiplier 20 generates an alarm signal when battery output voltage drops below the preset limit, say 7.0 volts. It also shuts the system down if the output voltage falls below the present limit of approximately 6.0 volts. These limits are for a 9 volt alkaline battery, the limits will change for a battery with a different voltage.

The analog/digital converter 92 converts the signal from the signal generating circuit 60 so that the patient can read it. The analog/digital converter 92 reads the level of output and converts it to the appropriate signal for the four gate integrated circuit which uses that signal to turn on the appropriate sequence of four LEDs 110.

Finally the impedance detector 160 is used to determine if the system is being used on a person (as opposed to someone just running the system without attaching it to a person).

Figure 3:
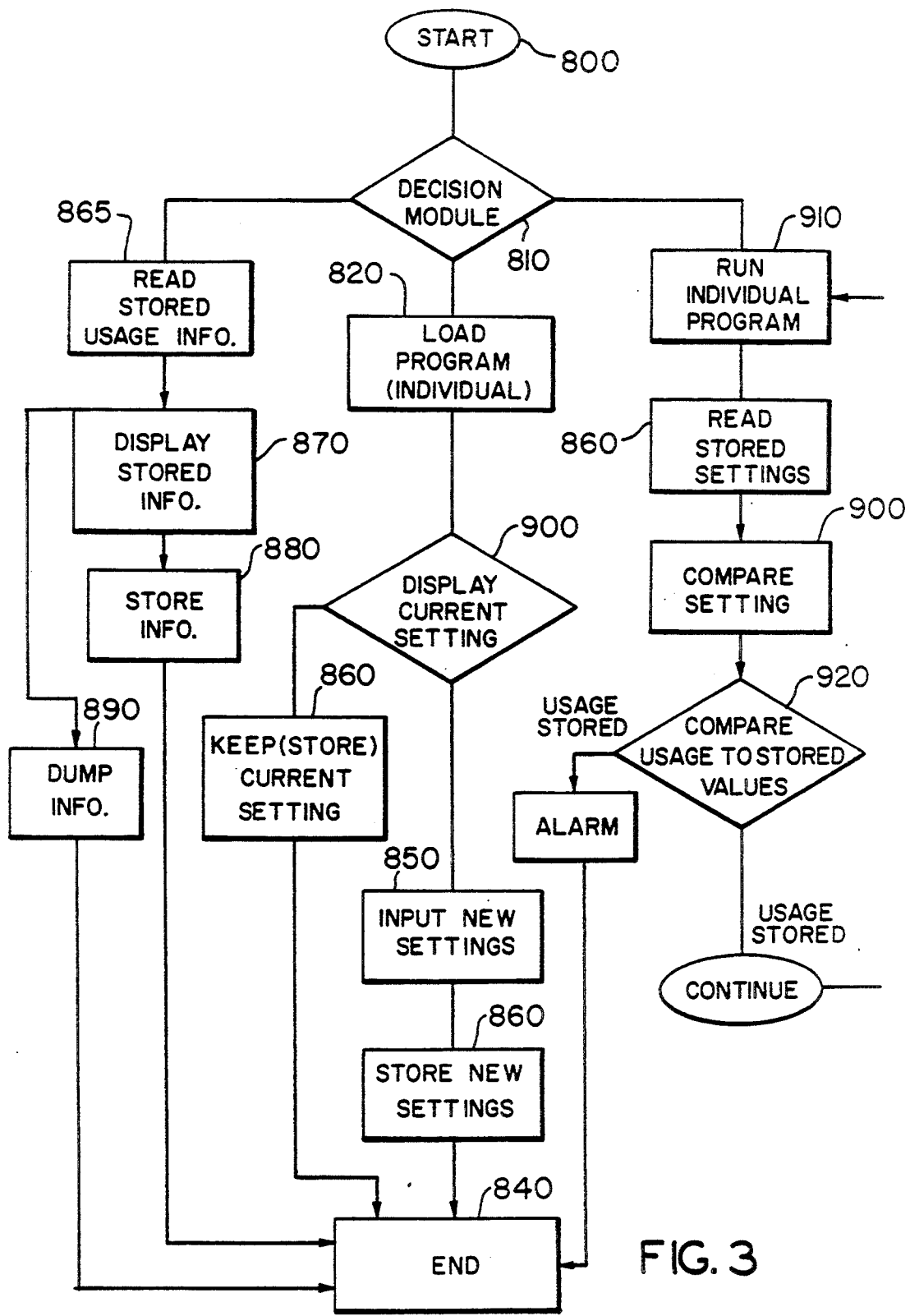
FIG. 3 is a logic flow chart of the data processing program controlling the operation of the apparatus of FIG. 2.

Referring now to FIG. 3, which is a flow chart of the timer unit 90 which the apparatus will use to monitor usage by the patient. This program will prevent the patient from misusing the apparatus and will allow the physician to set an individual treatment program and to monitor the patient's compliance to the set program.

The timer unit 90 will allow the therapist to set the number of days the system is to be used, the number of times per day the system will be used and the time duration for each use.

The program will start 800 with an Origination Decision module 810. The Origination Decision Module 810 will give the therapist three choices for use. If the Individualized Program 820 pathway is chosen, the timer unit will load the Individualized Program 820. Then the Individualized Program 820 will begin with a display showing the Current Setting 900, for each of the parameters (i.e. the number of days of use, the number of times per day of use and the length of time for each use). Next the program will ask the therapist whether he wants to Keep the Current Settings 900, or Input New Settings 830. If the therapist wishes to use the same settings as are already registered in the program, the Individualized Program 820, will Store 860 the values and will End 840. However, if the therapist wishes to change the settings, the program will proceed to the Change Input Values 850 module in which the computer will ask the therapist for the new values for the settings. Then the computer will Store 860 the new values and will End 840.

Another selection which a therapist may make at the Origination Decision Module 810 is to read the stored information from the patient's system. If the therapist decides to access the Read Stored Results 865 module, the Setting and Use information will be displayed 870, and the therapist will decide whether to store the patient information in the Patient Storage Module 880, or else it will Dump the information 890 and it will End 840.

A final selection which the therapist may access through the Origination Decision Module 910, is actually to use the system. If this choice is the inputted selection, the Run Timed Program 910 will be initialized. The Run Timed Program 890 will read the stored 860 values. Then the program will Check 920 the Stored 860 values against the Current Running Settings 900 which is the values of the Run Timed Program 890 for this usage of the system. If the Current Running Settings 900 for the number of days of use is greater than the Stored 860 values, the program will End 840 without the system being turned on. Next, the Run Timed Program 890 will check the value of the Stored 890 values for the number of uses for a given day and if the Current Running Settings 900 is greater than the Stored 890 values for number of uses for a day, the system will End 840 for that day and the system will not be able to be used until the next day. Finally, as the system is being used, a Running Time Clock will be compared to the Run Timed Program, 890, and when the Current Running Settings in 900 is greater than the Stored 890 values for the length of time for that session, the system will End 840 for that session and the system will not be able to be used until the next session period.

In FIG. 4 the chart demonstrates the effect of the inventive apparatus on the ACTH, cortisol, beta endorphin and serotonin, biochemical neurotransmitters. Multiple tests were made on three normals and other normal volunteers in the office using monopolar, bipolar and placebo instruments on a double blind basis. The symbol "n" denotes how many samples were made for each type of test. All tests for two of the three normals were made at the same time of day, the third normal was done always at 8 a.m. each morning and the 10 volunteers were processed at 10 a.m. to 12 noon for all their testing.

As is shown in the chart, the results on the tested neurotransmitters were marked. In each, the bipolar application had the greater effect on the neurotransmitter, with the monopolar still having significant results in its own right.

Turning to the improved invention relating to iontophoretic transdermal delivery, the present invention is applicable to the topical delivery of virtually any pharmaceutical agent which has a charge or can be formulated in a carrier such that the molecule has a charge or a dipole. As is commonly known in techniques which use electrokinetic phenomenon, such as electrophoresis and electroosmosis, a charge species will tend to migrate in a medium depending on the relationship of the charge on the species to the charge applied to the medium. For example, when it is desirable to use a certain drug having a negative charge, the drug in an appropriate carrier is applied topically to the area to be treated and the negative electrode (of the foregoing apparatus) is applied in contact with the same patient area. Because the negatively charged drug will be repelled by the negative electrode, the drug will migrate away from the electrode, and thus transdermally into the patient's tissues.

Although a bipolar waveform can be used, it is important to note that the present invention when used for iontophoretic delivery most preferably provides a waveform which is exclusively monopolar. This arrangement is in contrast to the teachings of the prior art, such as Sibalis, which teach the use of alternating current. We have found that the use of a monopolar waveform, such as that shown in FIG. 1D, provides improved transdermal deliver by virtue of the avoidance of a reversal in polarity which will tend to reverse or slow the transdermal delivery of the drug. Additionally, the use of a monopolar complex waveform allows for reduced electrical energy to be applied to the patient to achieve a particular dosage; especially since additional energy is not required to compensate for the application of an alternating current waveform which impedes the transdermal delivery. It would be permissible to provide a waveform having a minor component which is a reversal of the monopolar component provided that the alternating current portion of the complex waveform is minimized; the benefits derived from the alternating current signal as described for the neuroaugmentive apparatus can be utilized in the delivery device but must be balanced with the preferred monopolar signal for delivery of the charged pharmaceutical species.

The present invention is applicable to the delivery of a wide variety of pharmaceutically active agents, including anti-inflammatory agents like cortizone, insulin, nicotine and nitroglycerin, some of which are commonly used in transdermal patches.

By the term "topical" is meant the direct iontophoretic administration of the pharmaceutical agent, whether on the surface is the skin (dermis), eye, gum or anywhere on the body on which electrodes can be conveniently located.

The present invention also has significant use in the iontophoretic delivery of psychoactive and neuroactive agents. As described previously and shown in FIG. 4, the neuromodulating apparatus can change the levels of serotonin, beta-endorphin, GABA, and other neural transmitters and controlling molecules. Accordingly, the administration of an analgesic if not a psychoactive or neuroactive agent can be further enhanced by the synergistic change in such neurotransmitters.

When the apparatus is used for iontophoretic delivery, a monopolar signal is more preferred. The carrier frequency (e.g., as shown in FIG. 1A) ranges from about 1 Hz to about 300 GHz, and facilitates the penetration of the total electrical signal; more preferably the carrier signal ranges from about 10 Hz to about 100 KHz, and most preferably ranges from 10–50 KHz. The first modulating signal is the "bio-active" frequency which, without desirous of being constrained to any particular theory, is believed to enhance the neurobiochemical levels in both the cerebral spinal fluid and in the blood plasma, such as by altering the permeability of synapses and other cellular membranes to various ions. This first modulating signal ranges from about 10 Hz to about 199 KHz, more preferably from about 10 Hz to about 50 KHz, and most preferably is in the range of 10–100 Hz. The second modulating signal is analogous to a "tuning" frequency and can be used to reduce the aggregate energy delivered to the patient during the "on" portion of the duty cycle. The second modulator ranges from 100 Hz to 300 GHz, more preferably from 100 Hz to 100 KHz, and most preferably in the range of 100–1,000 Hz. A preferred embodiment of the iontophoretic delivery device uses a carrier signal of about 15 Khz, a first modulator of about 10 Hz, and a second modulator of about 500 Hz.

Additional modulating frequencies may be used, depending on the application. Preferably, these additional modulating frequencies will operate at the resonant frequency of a particular tissue type. You could have N modulators in this application.

The particular drug or combination of drugs to be administered is provided in a suitable carrier by methods well-known to the artisan. It is preferable to formulate a solution of the drug for delivery through moist electrodes which are commonly used and available, and analogous to those described by Sibalis. It is preferred to use a penetration enhancer such as SEPA ™ available from MacroChem Corporation, Massachusetts. Other suitable penetration enhancers can include wetting agent type molecules and mixtures thereof.

The embodiment of the above description has been based on discrete components to enhance the understanding of the functional characteristics of the system. Numerous modifications and adaptations thereof will be readily apparent to those skilled in the art without departing from the spirit and scope of the present invention.

What is claimed is:

1. In combination, in a system for the iontophoretic topical delivery of a pharmaceutically active agent, said system comprising:
   a. means for generating a substantially constant current pulsed DC output voltage;
   b. means for converting said output voltage into a double modulated output adjustable constant current waveform;
   c. contact means for containing and delivering said pharmaceutically active agent to a topical area of a patient in need of treatment, said contact means including at least two electrodes;
   d. means for directing said double modulated output waveform to said contact means;
   wherein said double modulated output waveform comprises a first waveform component ranging between 1 Hz and 300 GHz, a second waveform component ranging between 10 and 199,000 Hz, and a third waveform component ranging between 100 Hz and 300 GHz, and each waveform component is substantially time invariant and distinct from said other waveform components, said double modulated output waveform having a monopolar characteristic.

2. The system of claim 1 wherein said first waveform component has a 50% duty cycle, and said second waveform component has a 75% duty cycle but not limited thereto.

3. The system of claim 1, wherein the first waveform component ranges from about 10 Hz to about 100 KHz.

4. The system of claim 3, wherein the first waveform component ranges from about 10–50 KHz.

5. The system of claim 4, wherein said second waveform component ranges from about 10 Hz to about 199 KHz.

6. The system of claim 1, wherein said third waveform component ranges from about 100 Hz to about 100 KHz.

7. The system of claim 1, wherein said first waveform component is approximately 15,000 Hz, said second waveform component is approximately 15 Hz, and said third waveform component is approximately 500 Hz but not limited thereto.

8. The system of claim 1, further comprising at least one additional waveform component operating at the resonant frequency of a particular tissue type, which is substantially time invariant and distinct from said other waveform components.

* * * * *